United States Patent
Ziglioli

(10) Patent No.: US 8,981,498 B2
(45) Date of Patent: Mar. 17, 2015

(54) ELECTRONIC MEMS DEVICE COMPRISING A CHIP BONDED TO A SUBSTRATE AND HAVING CAVITIES AND MANUFACTURING PROCESS THEREOF

(75) Inventor: Federico Giovanni Ziglioli, Pozzo d'Adda (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 140 days.

(21) Appl. No.: 13/467,456

(22) Filed: May 9, 2012

(65) Prior Publication Data

US 2012/0286381 A1 Nov. 15, 2012

(30) Foreign Application Priority Data

May 10, 2011 (IT) .............. TO2011A0408

(51) Int. Cl.
*H01L 29/84* (2006.01)
*H01L 21/02* (2006.01)
*B81C 1/00* (2006.01)

(52) U.S. Cl.
CPC .... *B81C 1/00182* (2013.01); *G01N 2291/0256* (2013.01); *B81B 2201/0214* (2013.01); *B81C 2203/019* (2013.01); *B81C 2203/032* (2013.01)
USPC 257/415; 438/53; 257/E29.324; 257/E21.002

(58) Field of Classification Search
None
See application file for complete search history.

(56) References Cited

U.S. PATENT DOCUMENTS

| 5,490,034 A | 2/1996 | Zavracky et al. |
| 8,499,613 B2 * | 8/2013 | Ziglioli et al. ............. 73/23.34 |
| 2002/0115198 A1 | 8/2002 | Nerenberg et al. |
| 2005/0049499 A1 * | 3/2005 | Kaplan ..................... 600/438 |
| 2006/0260408 A1 | 11/2006 | Villa et al. |
| 2008/0246723 A1 | 10/2008 | Baumbach |
| 2010/0170324 A1 | 7/2010 | Mastromatteo et al. |
| 2011/0209524 A1 * | 9/2011 | Ziglioli et al. ............. 73/23.34 |
| 2011/0318840 A1 | 12/2011 | Ziglioli et al. |

FOREIGN PATENT DOCUMENTS

WO WO 03067945 A1 * 8/2003
WO 2010109363 A2 9/2010

* cited by examiner

*Primary Examiner* — Ori Nadav
*Assistant Examiner* — Ernest Allen, III
(74) *Attorney, Agent, or Firm* — Seed IP Law Group PLLC

(57) ABSTRACT

An electronic MEMS device is formed by a chip having with a main face and bonded to a support via an adhesive layer. A cavity extends inside the chip from its main face and is closed by a flexible film covering the main face of the chip at least in the area of the cavity. The support has a depressed portion facing the cavity and delimited by a protruding portion facing the main face of the chip. Inside the depressed portion, the adhesive layer has a greater thickness than the projecting portion so as to be able to absorb any swelling of the flexible film as a result of the expansion of the gas contained inside the cavity during thermal processes.

17 Claims, 3 Drawing Sheets

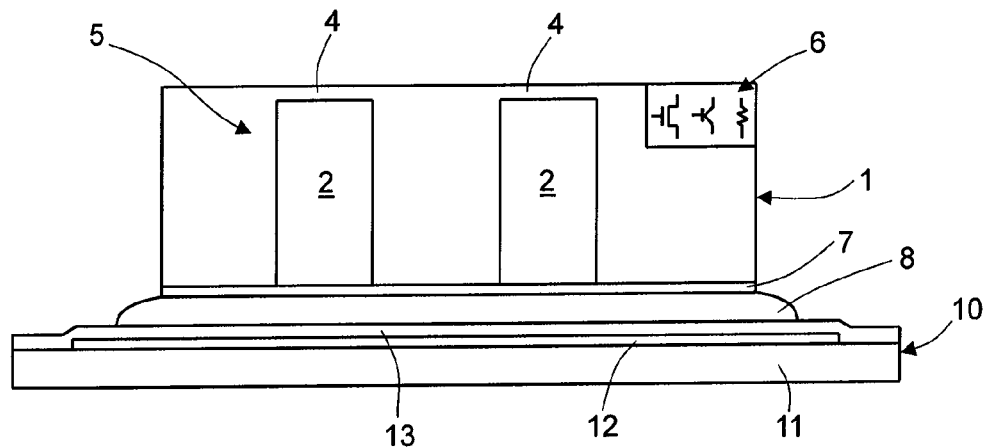
Fig.1 *(Prior Art)*
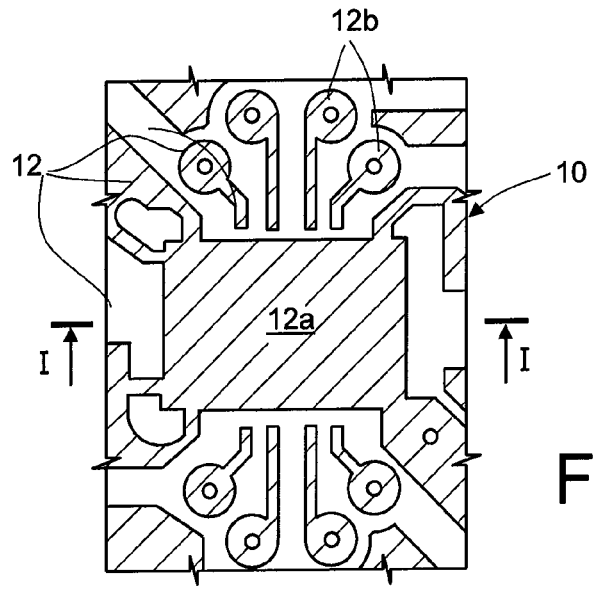
Fig.2 *(Prior Art)*
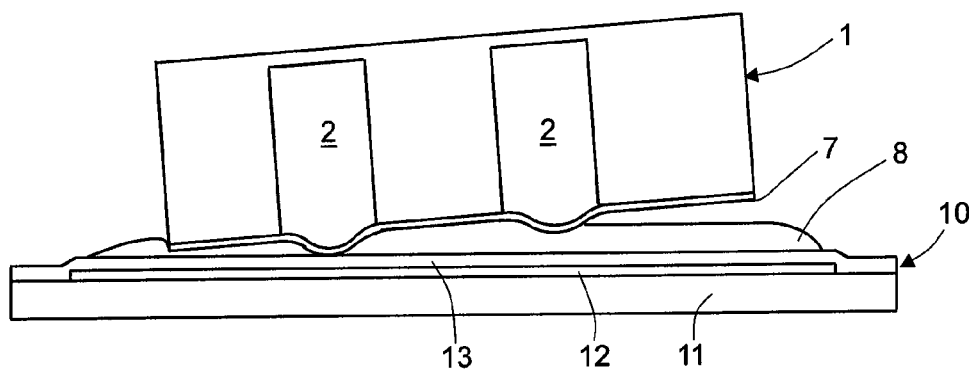
Fig.3 *(Prior Art)*

ELECTRONIC MEMS DEVICE COMPRISING A CHIP BONDED TO A SUBSTRATE AND HAVING CAVITIES AND MANUFACTURING PROCESS THEREOF

BACKGROUND

1. Technical Field

The present disclosure relates to an electronic micro-electro-mechanical system (MEMS) device comprising a chip bonded to a substrate and having cavities and to the manufacturing process thereof. In particular, the present disclosure applies to chemical sensors for detecting odorous matters.

2. Description of the Related Art

As is known, in devices for recognizing odorous matters (such as the one described, for example, in U.S. patent application Ser. No. 12/648,996, published as U.S. Application Publication No. 2010/0170324, and incorporated herein by reference in its entirety) the semiconductor material chip accommodates one or more cavities delimiting respective membranes carrying, i.a., respective adsorbent layers. Each membrane and the respective adsorbent layer form part of an oscillating circuit having electrical characteristics that vary with the weight of the ensemble including the membrane, the adsorbent layer, and any possible adsorbed material, enabling detection and possibly the amount of the adsorbed material.

Membranes may be manufactured using various techniques, some of which envisage formation of cavities extending on one side of the chip. In this case, when the chip is bonded on a substrate, the cavities are to be kept clean without being contaminated with glue or any other material.

FIGS. 1-3 show, for example, a chip 1 fixed to a substrate 10. The chip 1 has a plurality of cavities 2, each delimiting at the top an own membrane 4 formed in the same monolithic semiconductor material as the chip 1. When the chip 1 forms a sensor for detecting odorous matters or in general a device for detecting chemical matters, each cavity may have, for example, a width of 250-300 µm and a depth of 500 µm, and the cavities may be made arranged at a mutual distance of 150-400 µm. In this case, the area of the membranes forms a sensitive region 5, and electrodes and other sensitive layers, such as adsorbent layers (not shown), are formed on top of the membranes 3, whereas a circuitry area 6, shown only schematically in FIG. 1 and including electronic components, extends on the side of the sensitive area 5, for example, according to U.S. patent application Ser. No. 12/648,996.

An adhesive layer or film 7, for example a die-attach film, is applied to the rear side of the chip 1 in order to close the cavities 2 at the bottom and prevent contamination thereof. The adhesive film 7 may be laminated on the back and cured using a thermal process so as to seal and protect the cavities.

A glue layer 8 fixes the chip 2, through the adhesive film 7, to the substrate 10. The substrate 10 may be of any type; for example, it may be formed by a printed-circuit board, comprising a core region 11 overlaid by at least one conductive layer 12, typically a copper layer, covered by a dielectric layer 13, typically a solder-mask layer. The conductive layer 12 is shaped so as to form conductive regions and connections, as shown, for example, in the top plan view of FIG. 2. Here, the conductive layer comprises a quadrangular region 12a of an area slightly greater than that of the chip, and connection regions 12b.

This type of attachment entails, however, problems. In fact, during bonding, when the structure undergoes thermal treatments, for example during the polymerization of the glue (carried out typically at 100-190° C.), since the air in the cavity 2 cannot exit and increases in volume, it exerts a pressure on the adhesive film 7 and the glue layer 8, which are yielding. Swellings are thus created that tend to raise the chip and, in particular in presence of lack of uniformity, can cause tilting of the chip 1 and delaminating of the glue layer.

The consequence thereof is that the yield of the assembly process is low, even lower than 50%.

The same problem applies to other types of MEMS devices, having cavities closed by sealing layers of compliant material and/or bonded on areas of compliant material.

BRIEF SUMMARY

Some embodiments of the present disclosure provide a device and a method that overcome the drawbacks of the prior art.

According to some embodiments of the present disclosure, there are provided an electronic device and the manufacturing process thereof, as defined in claims 1 and 12, respectively.

In practice, in the support, underneath the area of the chip where the cavities are formed, there is a depressed portion containing part of the glue. During the thermal treatments, the glue, being compliant, allows for expansion of the air in the cavities within the depressed area, thus preventing raising and/or tilting of the chip with respect to the substrate. Typically, the depressed portion comprises a recess formed by the surface layers of the support. In addition, spacer elements may extend within the glue layer so as to ensure the thickness of the swelling to be always smaller than the distance between the chip and the plane underlying the chip itself and to ensure planarity of the chip.

BRIEF DESCRIPTION OF THE SEVERAL VIEWS OF THE DRAWINGS

For a better understanding of the present disclosure, preferred embodiments are now described, purely by way of non-limiting example, with reference to the attached drawings, wherein:

FIG. 1 is a cross-section through a chip having cavities and bonded to a substrate;

FIG. 2 is a top plan view of the substrate of FIG. 1;

FIG. 3 shows the chip of FIG. 1 in case of tilting and delamination;

DETAILED DESCRIPTION

Figure 4:
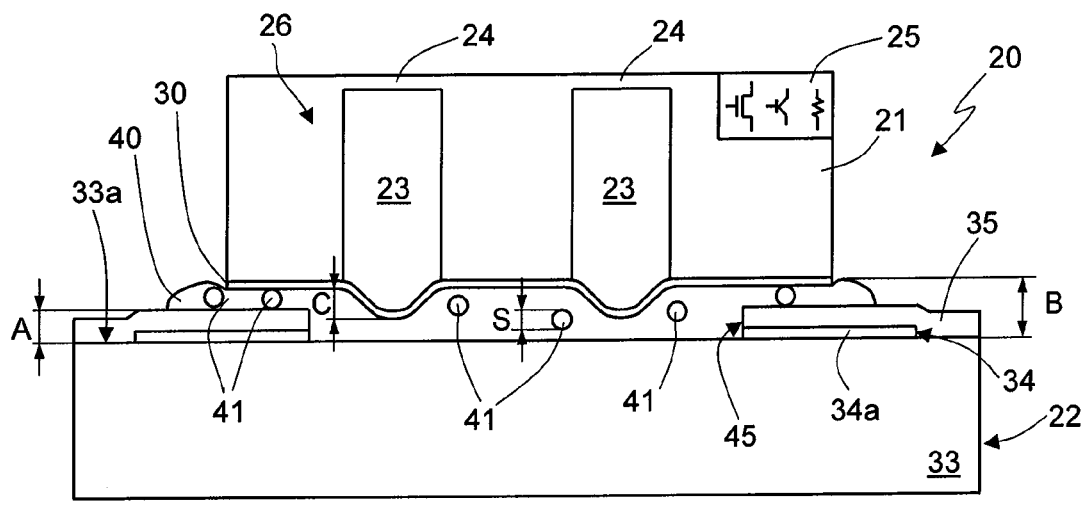
FIG. 4 shows a cross-section of the present device.
Figure 5:
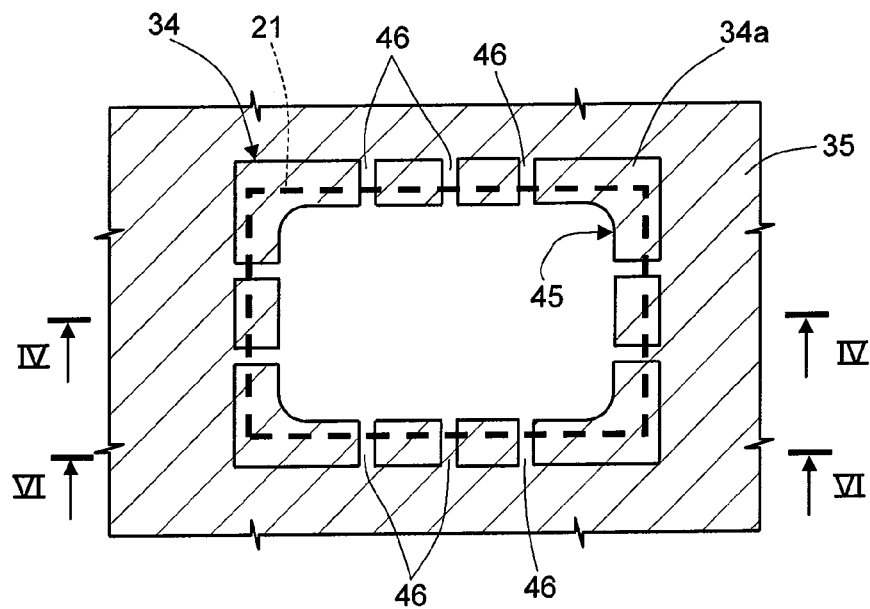
FIG. 5 is a top plan view of the device of FIG. 4.
Figure 6:
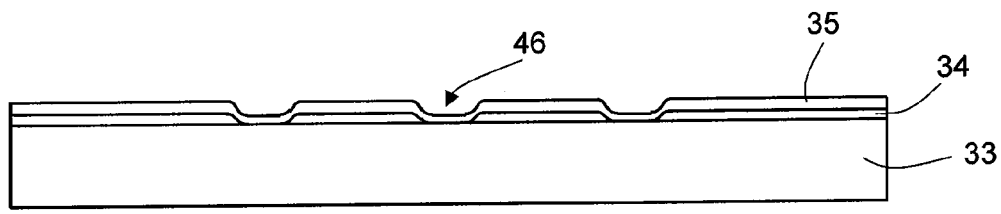
FIG. 6 shows a cross-section, taken along section line VI-VI of FIG. 5.

FIGS. 4-6 show an electronic device 20 including a chip 21 bonded to a substrate 22 by a glue layer 40. The chip 21 has cavities 23 extending from the rear surface of the chip 21 and delimiting membranes 24 at the bottom. If the electronic device 20 forms part of a chemical sensor, adsorbent layers (not shown) may be formed on the membranes 24 and may be of a material able to bind with the chemical substance to be detected, as described in detail in aforementioned patent application U.S. patent application Ser. No. 12/648,996. For example, the adsorbent layers can contain metal-porphyrins having an affinity with the chemical matters to be detected and form, together with the membranes 24, a sensitive area 26. For the rest, the chip 21 may comprise a circuitry area 25 including electronic components (shown schematically) so as to form, with the sensitive area 26, a device for detecting chemical matters, for example, odorous chemical matters.

An adhesive film 30 covers the rear surface 21a of the chip 21 and closes one or more cavities 23 at the bottom. The adhesive film 30 may be a die-attach film, for example, of epoxy material having a thickness of 10-50 µm, laminated on the rear surface 21a.

The substrate 22 comprises a base layer 33 having a surface 33a covered by a conductive layer 34 and a protective layer 35, for instance of insulating material, arranged on top of the conductive layer. For example, the substrate 22 may be formed by a printed-circuit board, and in this case the base layer 33 may be a core layer, the conductive layer 34 may be a metal material layer, such as copper, and the protective layer 35 may be a solder-mask layer. The core layer 33 is of an organic material, for example BT (bismaleimide triazine), epoxy resin, FR-4 (Flame Retardant 4), LCP (Liquid Crystal Polymer), or polyimide.

In the example shown, part of the conductive layer 34 and part of the protective layer 35 are removed so as to form a recess 45 extending at least underneath the area of the cavity or cavities 23, as shown in FIG. 4, and having an area smaller than the area of the chip 21, in top plan view. In practice, here the conductive layer 34 is shaped so as to form, i.e., an ring-shaped region 34a and its width $d_e$ (distance between the inner and the outer edges of the ring) is such that the lateral surface of the chip 21 falls, in top plan view, inside the ring-shaped region 34a. In other words, the external edge of the ring-shaped region 34a delimits a greater area than the area of the main face of the chip, in top plan view.

In the embodiment of FIG. 4, moreover, the glue layer 40 incorporates spacer elements 41, for instance balls of insulating or conductive material. For example, the spacer elements 41 may be of a polymeric material, such as polytetrafluoroethylene (PTFE), or glass, metal material, such as silver, and the like, and the glue may be of a polymeric material, such as an epoxy resin or a silicone material, or in any case of a softer material than the spacer elements 41, the support 22, and the chip 21.

The spacer elements 41 preferably all have substantially the same preset thickness so as to ensure a plane rest for the chip 21.

In particular, by designating by A the depth of the recess 45 (sum of the thicknesses of the conductive layer 34 and of the protective layer 35), by S the diameter or thickness of the spacer elements 41, by C the expected thickness of the swelling that forms underneath the cavities 23 because of thermal effect, and by B the distance between the bottom surface 21a of the chip 21 and the surface 33a of the base layer 33 (neglecting the thickness of the adhesive film 30), the dimensions are chosen so that:

$$B = A + S > C \tag{1}$$

Generally, with current manufacturing techniques, C is approximately 10% of the depth of the cavities 23. With cavities 23 having a depth of 500 µm, C is thus normally comprised between 40 and 60 µm, and on average is approximately 50 µm.

In case of a printed-circuit board, with a thickness of the copper conductive layer 34 of 15-20 µm and a thickness of the protective layer 35 of 30-50 µm, the thickness A is typically comprised between 45 and 70 µm, for example 50 µm.

To satisfy Eq. (1), it is thus sufficient to use spacer elements 41 having a diameter of 25 µm. According to the application, materials, and dimensions of the various parts, the spacer elements 41 may, however, have typical thicknesses of 10, 15, 20, 25, 30, 50 µm or even 100 µm.

The recess 45 may be coupled to trenches 46 extending peripherally from the recess 45 throughout the width of the ring 34. In practice, as may be seen in FIG. 6, in the area of the trenches 46 the conductive layer 34 is removed. For example, the trenches 46 may have a width of 100-200 µm and be arranged at a distance from one another of 300-500 µm.

In this way, during fabrication, after application of the glue on the chip 21 or on the substrate 20, also because the glue 40 is soft, it is possible to cause any possible air trapped underneath the chip 21 to exit, thus eliminating a source of disturbance during bonding. In practice, the trenches 46 form venting channels.

The recess 45 and the trenches 46 may be formed while defining the conductive layer 34 and the protective layer 35, with a standard photolithographic technique, in a simple and inexpensive way. Alternatively, they may be formed at the end of the manufacturing of the substrate 22, prior to bonding, using a specific milling operation. In this latter case, it is possible to remove just part of the conductive layer 34 or, if the protective layer 35 is sufficiently deep, to remove only the protective layer 35.

The device described herein has numerous advantages.

By virtue of a depressed area or recess underneath the chip 21, at least in the area of the cavities 23, the air can expand during the thermal cycles and form swellings without causing raising of the chip from the nominal position. In fact, the chip always rests on a surface of constant thickness, guaranteed by the spacer elements 41. Any air possibly trapped therein can exit from the trenches 46.

In this way, any tilting of the pads and delamination of the glue layer or of the film 30 are prevented, and a yield of the assembly process higher than 80% is obtained.

Moreover, the recess 45 forms a side delimitation of the area subject to deformation, ensuring a good structural and conformational stability of the finished device.

Manufacturing and bonding may be carried out without additional costs as compared to the device of FIGS. 1-3 if the recess is formed while manufacturing the substrate 22, by simply modifying the design of the structures, without requiring specific operations during production of the substrate or in the assembly process.

The performances of the device are not affected by the assembly.

Figure 7:
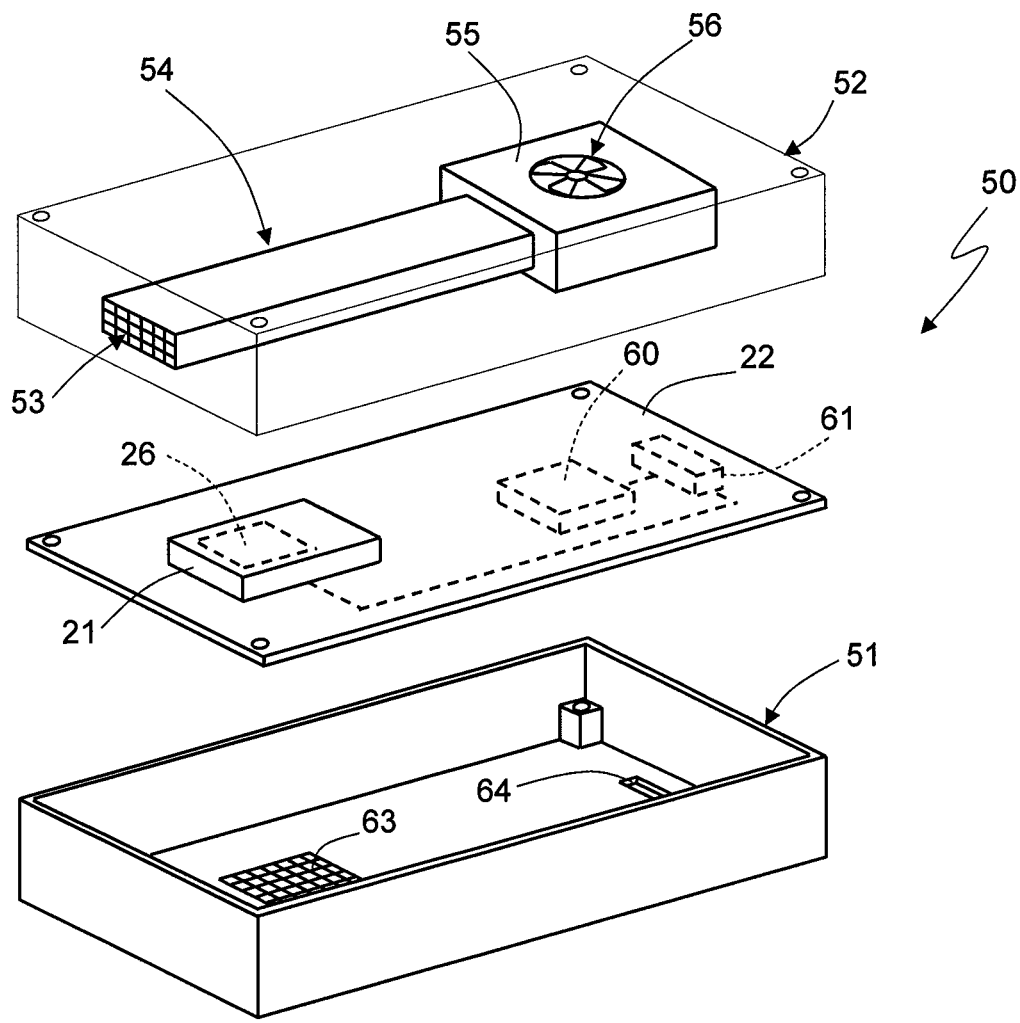
FIG. 7 shows an integrated chemical sensor for detecting odorous matters, incorporating the present device.

FIG. 7 shows an integrated chemical sensor 50 for detecting odorous matters that may incorporate the device 20. The chemical sensor 50 is formed, for example, as described in U.S. patent application Ser. No. 13/016,086 filed on Jan. 28, 2011, published as U.S. Application Publication No. 2011/0209524, and incorporated herein by reference in its entirety. The chemical sensor 50 comprises a casing formed by a base 51 and by a lid 52, enclosing the printed-circuit board that forms the support 22.

The lid 52 (represented in ghost view) has an input port 53 for introduction of gases to be analyzed and defines a channel 54 extending from the input port 53 to a suction fan 55, in turn connected to an output port 56.

The channel 54 extends on top of the chip 21, bonded on the side of the support 22 facing the lid 52 so that the gases entering the channel 54 for the suction of the fan 55 lap the chip 21, and the odorous matters to be recognized are captured in the sensitive area 26.

The support 22, on the side opposite the chip 21, carries other components, such as, for example, a fan-control device 60, coupled via conductors (not shown) to the fan 55, and an auxiliary chip 61, for example a controller with memory, a signal-processing circuit, or the like. In turn, the auxiliary chip 61 may be coupled to an external data-processing apparatus (not shown).

The base 51, which is to couple with the lid 52 so as to enclose the support 22 in between, has an input 63 and an output 64 for coolant air.

Finally, it is clear that modifications and variations may be made to the device and the manufacturing process described and illustrated herein, without thereby departing from the scope of the present disclosure.

In particular, the depressed area may be formed in a surface layer of the substrate, creating a local recess or depressed area where a glue layer can accumulate and which has a greater thickness than the neighboring areas so as to contain expansion and swelling of the air in the cavities.

The spacer elements 41 may have a shape other than the spherical shape; they may, for example, be spheroidal, even irregular, with projections, for example shaped as flakes, but in any case preferably able to ensure a constant distance from the underlying layer of the chip, for example as a result of a preferential lie position that may be achieved during application of the glue layer or by compression during application of the chip.

The conductive region 34 underneath the chip 21 may have a shape different than the annular shape shown; for example, it may be formed by portions of any shape set alongside one another, or else delimit a plurality of recesses, one for each cavity 23 of the chip 21 or may even be absent.

Finally, the chemical sensor may be made differently, for example for analysis of matters in a liquid, as described in U.S. patent application Ser. No. 13/170,058, which published as U.S. Application Publication No. 2011/0318840, is incorporated herein by reference in its entirety, and discloses a support that is not completely contained in the casing of the chemical sensor.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electronic MEMS device comprising:
a chip having a main face,
a cavity extending inside the chip from the main face;
a flexible film covering at least a portion of the main face of the chip adjacent to the cavity;
a support; and
an adhesive layer sandwiched between the flexible film and the support for fixing the chip to the support, wherein the support includes:
a depressed portion facing the cavity and a protruding portion facing the main face of the chip the protruding portion delimiting the depressed portion, wherein the adhesive layer has a greater thickness inside the depressed portion than on the protruding portion;
a printed circuit board:
a base body having a surface and a core layer. and
a multi-layered structure for on top of the surface of the base body wherein the depressed portion is formed by a recess in the multi-layered structure, the recess accommodating part of the adhesive layer, the multi-layered structure including a shaped metal layer, extending on top of the surface of the base body, and a protective layer covering the shaped metal layer, the shaped metal layer and the protective layer forming the protruding portion delimiting the depressed portion.

2. A device according to claim 1, wherein the shaped metal layer comprises a generally ring-shaped region having an inner edge delimiting the recess and an outer edge delimiting an area that is bigger than the area of the main face of the chip.

3. A device according to claim 2, wherein the generally ring-shaped region has a plurality of trenches or channels extending between the inner and the outer edges.

4. A device according to claim 1, further comprising spacer elements positioned in the adhesive layer.

5. A device according to claim 4, wherein the adhesive layer is of a softer material than the spacer elements, the support and the chip.

6. A device according to claim 4, wherein the adhesive layer is formed by an epoxy or silicone glue and the spacer elements are made of a polymeric material, glass or metal.

7. A device according to claim 4, wherein the spacer elements have a spheroidal shape.

8. An electronic MEMS device comprising:
a chip having a main face,
a cavity extending inside the chip from the main face;
a flexible film covering at least a portion of the main face of the chip adjacent to the cavity;
a support; and
adhesive layer sandwiched between the flexible film and the support for fixing the chip to the support, wherein the support includes:
a depressed portion facing the cavity and a protruding portion facing face of the chip. the protruding portion delimiting the depressed portion, wherein the adhesive layer has a greater thickness inside the depressed portion than on the protruding portion, wherein:
the support comprises:
a base body having a surface, and
a multi-layered structure formed on top of the surface of the base body, wherein the depressed portion is formed by a recess in the multi-layered structure, the recess accommodating part of the adhesive layer;
the adhesive layer incorporates spacer elements; and
the chip and the surface of the base body are separated by a distance given by a sum of thicknesses of the multi-layered structure and of the spacer elements.

9. A device for detecting odorous matters comprising:
a casing having a channel for a gas to be analyzed and a motor for advancing the gas to be analyzed; and
an electronic MEMS device carried by the casing, the MEMS device including:
a chip having a main face and including a sensitive region of a material able to bind with target chemicals in the gas to be analyzed;
a cavity extending inside the chip from the main face;
a flexible film covering at least a portion of the main face of the chip adjacent to the cavity;
a support; and
an adhesive layer sandwiched between the flexible film and the support for fixing the chip to the support,
wherein the support has a depressed portion facing the cavity and a protruding portion facing the main face of the chip, the protruding portion delimiting the depressed portion, wherein the adhesive layer has a greater thickness inside the depressed portion than on the protruding portion, wherein the support comprises:
a base body having a surface, and a multi-layered structure formed on top of the surface of the base body, wherein the depressed portion is formed by a recess in the multi-layered structure, the recess accommodating part of the adhesive layer.

10. A device according to claim 9, wherein:
the support comprises a printed circuit board;
the base body includes a core layer; and
the multi-layered structure comprises a shaped metal layer, extending on top of the surface of the base body, and a protective layer covering the shaped metal layer, the shaped metal layer and the protective layer forming the protruding portion delimiting the depressed portion.

11. A device according to claim 10, wherein the shaped metal layer comprises a generally ring-shaped region having an inner edge delimiting the recess and an outer edge delimiting an area that is bigger than the area of the main face of the chip.

12. A device according to claim 11, wherein the generally ring-shaped region has a plurality of trenches or channels extending between the inner and the outer edges.

13. A device according to claim 9, wherein the MEMS device includes spacer elements positioned in the adhesive layer.

14. A device according to claim 13, wherein the adhesive layer is of a softer material than the spacer elements, the support and the chip.

15. A device according to claim 13, wherein the adhesive layer is formed by an epoxy or silicone glue and the spacer elements are made of a polymeric material, glass or metal.

16. A device according to claim 13, wherein the spacer elements have a spheroidal shape.

17. A device according to claim 9, wherein:
the adhesive layer incorporates spacer elements; and
the chip and the surface of the base body are separated by a distance given by a sum of thicknesses of the multi-layered structure and of the spacer elements.

* * * * *

UNITED STATES PATENT AND TRADEMARK OFFICE
CERTIFICATE OF CORRECTION

| | |
|---|---|
| PATENT NO. | : 8,981,498 B2 |
| APPLICATION NO. | : 13/467456 |
| DATED | : March 17, 2015 |
| INVENTOR(S) | : Federico Giovanni Ziglioli |

It is certified that error appears in the above-identified patent and that said Letters Patent is hereby corrected as shown below:

In the Claims

Column 5, Line 57:
"portion facing the main face of the chip the protruding" should read as, --portion facing the main face of the chip, the protruding--.

Column 5, Line 61:
"a printed circuit board:" should read as, --a printed circuit board;--.

Column 5, Line 62:
"a base body having a surface and a core layer. and" should read as, --a base body having a surface and a core layer, and--.

Column 5, Line 63:
"a multi-layered structure for on top of the surface of the" should read as, --a multi-layered structure formed on top of the surface of the--.

Column 5, Line 64:
"base body wherein the depressed portion is formed by" should read as, --base body, wherein the depressed portion is formed by--.

Column 6, Line 29:
"adhesive layer sandwiched between the flexible film and" should read as, --an adhesive layer sandwiched between the flexible film and--.

Column 6, Line 33:
"portion facing face of the chip, the protruding portion" should read as, --portion facing the main face of the chip, the protruding portion--.

Signed and Sealed this
Twentieth Day of October, 2015

Michelle K. Lee
*Director of the United States Patent and Trademark Office*